United States Patent [19]

Alexanderson et al.

[11] 4,021,498
[45] May 3, 1977

[54] ADIABATIC PROCESS FOR NITRATION OF NITRATABLE AROMATIC COMPOUNDS

[75] Inventors: Verner Alexanderson, Plainfield; James Bryant Trecek, Bridgewater; Cornelius Marsden Vanderwaart, Basking Ridge, all of N.J.

[73] Assignee: American Cyanamid Company, Stamford, Conn.

[22] Filed: Dec. 9, 1975

[21] Appl. No.: 639,019

[52] U.S. Cl. .............................. 260/645; 260/646
[51] Int. Cl.$^2$ .................. C07C 79/10; C07C 79/12
[58] Field of Search ........................... 260/645, 646

[56] References Cited

UNITED STATES PATENTS

| | | | |
|---|---|---|---|
| 3,087,971 | 4/1963 | Samuelsen | 260/645 |
| 3,243,466 | 3/1966 | Brogden et al. | 260/645 |
| 3,928,475 | 12/1975 | Dassel | 260/645 |

Primary Examiner—Leland A. Sebastian
Attorney, Agent, or Firm—William J. van Loo

[57] ABSTRACT

An adiabatic process for the mononitration of nitratable aromatic hydrocarbons and halo substituted aromatic hydrocarbons which yield a mononitration product containing less than 500 ppm. of dinitrated product is disclosed.

9 Claims, No Drawings

ADIABATIC PROCESS FOR NITRATION OF NITRATABLE AROMATIC COMPOUNDS

This invention relates to an improved process for the mononitration of a nitratable aromatic compound. More particularly, it relates to an improved adiabatic process for the mononitration of a nitratable aromatic compound, and still more particularly to a continuous or batch adiabatic process for the production of nitrobenzene.

The nitration of nitratable aromatic compounds is old and well known. The nitration of benzene to mononitrobenzene is widely practiced commercially, particularly for the manufacture of aniline. Conventional commercial processes for nitrobenzene ordinarily utilize either a batchwise or continuous addition of a mixture of sulfuric acid and nitric acid, commonly referred to as mixed acid, to benzene. The nitration reaction is ordinarily conducted at a temperature in the range 60°–70° C. or lower and involves removal of heat by cooling. Mixed acids are used containing high nitric acid content, i.e. in the order of 20–30%, and as a result the volume of mixed acid is relatively low; ratio of mixed acid to benzene is ordinarily about 2.9–3.6 to 1. The spent acid, i.e., the mixed acid essentially completely depleted of nitric acid, generally about 70% sulfuric acid, is then reconcentrated to 93–95% sulfuric acid or fortified with sulfur trioxide or oleum to 100–105% for recycle and reuse.

One of the disadvantages inherent in the conventional processes, primarily the extensive cooling required to remove the heat of reaction, was recognized by Castner (see U.S. Pat. No. 2,256,999) who disclosed an adiabatic nitration process in which the total heat of mixing and heat of reaction was retained and utilized in the reaction to increase the rate thereof and also to raise the temperature of the spent acid to a peak of about 110° C., thereby permitting more efficient concentration of the spent acid by conventional means, such as flash evaporation.

The Castner process for the nitration of benzene is conducted with the reactants at an initial temperature of approximately 90° C. This is a temperature appreciably higher than the boiling point of benzene, and thus unless the benzene is added slowly, or the entire reaction system is under pressure, benzene would boil violently and thus disrupt the reaction. If the benzene is added slowly, the amount of dinitrobenzene produced increases. This result is illustrated by Example 17 in which the conditions of the Castner process are shown to yield nitrobenzene containing appreciable quantities of dinitrobenzene. It is, of course, possible to have a high initial reaction temperature without creating an excessive final temperature if the amount of nitric acid in the mixed acid is small. This technique, however, leads to inconveniently large volume of reactants and does not represent a practical solution. Even if an aromatic material with a boiling point greater than 90° C. is being nitrated, the high starting temperature of Castner process is a disadvantage because if a reasonable amount of nitric acid (i.e., more than about 5%) is used in the reaction mixture, the temperature of the final reaction mixture will be excessive. If the final reaction mixture is too hot, not only will side reactions be likely to occur, but the reaction may be hazardous as well. Insofar as we are aware, the adiabatic nitration process has not met with commercial success, probably for these reasons.

It is desirable to minimize dinitro formation since their presence is potentially hazardous. Although dinitrophenol, for example, may be removed from nitrobenzene reaction mixtures by a simple alkaline wash, dinitrobenzene is not so readily removed therefrom. In fact, removal of dinitrobenzene requires distillation of the product mononitrobenzene therefrom, which can lead to high concentrations of dinitrobenzene in the still bottom, which is a potentially hazardous situation. Similar dinitrobenzene buildup may occur in any process where mononitrobenzene is vaporized, such as in catalytic vapor phase aniline processes. Such buildups may also occur during use or processing of other mononitro materials and present a sever risk of explosion or fire whenever they occur. There is need for an efficient process for the production of mononitro compounds which are relatively free of contamination with dinitro compounds. Because of the many advantages of an adiabatic nitration process, it would be particularly desirable to have an adiabatic process which delivered a product low in dinitro compounds.

It is an object of the present invention to provide a continuous or batch adiabatic process for the production of mononitro aromatic compounds containing less than 500 ppm of the dinitrated species thereof. It is yet another object of the present invention to provide such a process for the production of nitrobenzene. Other objects and advantages will be set forth in the following description of the invention.

In accordance with the above stated objectives we have now discovered an improved adiabatic process for the nitration of a nitratable aromatic compound, stable in the presence of hot sulfuric acid, which produces a mononitro compound containing less than 500 ppm of the dinitrated species thereof, which comprises continuously contacting a nitratable aromatic compound with a mixed acid reactant consisting of about 60–70% sulfuric acid, 5–8.5% nitric acid, and not less than 25% water at an initial temperature of about 40° C. to 80° C., for a period of time ranging from about 0.5 to 7.5 minutes, whereby the reaction temperature does not exceed about 145° C.

In order to insure complete denitration of the mixed acid, the aromatic nitratable compound is used in slight excess (about 1–10%) over the nitric acid, and preferably about 1–5%.

If the process of the present invention is conducted as a batch process, the nitratable aromatic compound is added with stirring to the mixed acid in an insulated vessel. It is desirable that the nitratable aromatic compound be added to the mixed acid as quickly as possible. When the nitration reaction has gone on for the desired period of time, the nitrated aromatic material may be separated from the mixed acid by standard methods. If the process of the present invention is conducted as a continuous process, a stream of the nitratable aromatic compound is contacted with a mixed acid reactant stream with adequate mixing and for the appropriate period of time to form a nitration reaction mixture which is separated into two streams, one stream consisting mainly of the mononitrated aromatic compound and the other stream consisting mainly of spent sulfuric acid. Whether the reaction is run as a continuous or batch process, however, the entire reaction mixture is appreciably warmed by the heat of the reaction, and this heat is useable to aid in the restoring of the sulfuric acid to its original concentration by removal of both the water formed in the nitration reaction, and the water in the nitric acid originally employed.

The process of the present invention has advantages over the method of Castner in that it utilizes initial reaction temperatures below the boiling point of the aromatic compound to be nitrated; it avoids the use of pressure or refluxing means; and controls the amount of water in the mixed acid, to an extent which minimizes dinitration.

As stated above, the mixed acid used in the process of this invention contains from about 5.0% to 8.5% nitric acid, preferably about 6.0% to 8.0% nitric acid; from about 60% to 70% sulfuric acid, preferably 62% to 68% sulfuric acid, and not less than about 25% water.

When the mixed acid contains less than about 5% nitric acid, the volume of mixed acid which must be handled becomes too high, i.e., the ratio of mixed acid to organic substrate is too high and becomes uneconomical. It will be understood, however, that the process of the invention is otherwise operable at lower than 5% nitric acid concentration. If the nitric acid concentration appreciably exceeds about 8.5% the nitration reaction tends to produce excessive amounts of dinitrated products (from an otherwise unnitrated organic species). When the nitration mixture contains about 60% to 70% sulfuric acid, the mixture (assuming essentially complete denitration thereof by the organic compound) will contain residual sulfuric acid (spent acid) having a concentration ranging from about 64% to 72%. We have found that when the spent acid concentration is appreciably less than about 64% sulfuric acid the nitration reaction is too slow and incomplete conversion results during the reaction times of the invention. On the other hand, when the spent acid contains appreciably more than 72% sulfuric acid, excessive dinitration results. Thus, we prefer to use a mixed acid which will result in a spent acid in the range 64–70% sulfuric acid.

A critical factor influencing the amount of dinitration is the amount of water in the mixed acid. We have found that if the mixed acid contains appreciably less than about 25% water, excessive dinitration will result. In particular, if the mixed acid contains less than about 25% water, nitration of benzene will result in greater than 500 parts per million of dinitrobenzene.

The reaction may be conducted at an initial temperature in the range of about 40° C to 80° C, depending on the nature of the organic substrate, provided that the heat generated thereby does not result in a peak temperature exceeding about 140–145° C. In the mononitration of benzene, we prefer to use an initial reaction temperature in the range of about 60° C. to 75° C.

To accomplish the mononitration reaction continuously in the shortest time, vigorous agitation is required to achieve intimate contact of the substrate and nitration medium. Vigorous agitation may be achieved by any means suitable, but can be defined generally as that degree of agitation which will result in completion of the nitration under the conditions described herein from about 0.5 to 7.5 minutes. Vigorous agitation is most important in conducting the nitration under conditions which result in the shortest reaction times. Preferably the reaction will be completed in about 0.5 to 3 minutes.

The process described herein for the mononitration of a nitratable aromatic compound will function with any aromatic hydrocarbon or halogen substituted aromatic hydrocarbon which is not degraded by hot sulfuric acid and whose nitration product is also stable in the presence of hot aqueous sulfuric acid, provided that the aromatic compound may be liquidified at a temperature within the range of about 40° to 80° C. Thus, the process may be used to produce mononitroderivatives of compounds such as benzene, toluene, dimethyl benzene, halobenzene, naphthalene, methylnaphthalene, halonaphthalene, halotoluene and halomethylnaphthalenes, etc. Hereafter, the term nitratable aromatic hydrocarbon shall refer to any aromatic hydrocarbon, or halo derivative of an aromatic hydrocarbon which is stable in the presence of hot sulfuric acid, liquifiable within the temperature range from about 40° to 80° C., and whose nitration product is also stable in the presence of hot aqueous sulfuric acid.

The process of the invention is not limited to any particular apparatus or assemblage thereof or to any particular method of operation. The reaction is preferably conducted continuously, ideally using a plug flow reactor. However, it may be carried in a series of staged reactors, or in a stirred cylindrical reactor.

The following examples are provided for illustrative purposes and may include particular features of the invention. However, the examples should not be construed to limit the invention, many variations of which are possible without departing from the spirit or scope thereof.

EXAMPLE 1

A reactant stream of benzene (1.1 molar proportions) and a reactant stream containing 5.2% nitric acid (1 molar proportion), 67.6% sulfuric acid and 27.2% water, were mixed and immediately metered at 68° C. into a vigorously agitated tubular reactor 40 inches in length and 1 inch in diameter. Residence time in the reactor was 4 minutes. The reaction stream at 116° C. exiting the reactor was allowed to separate and the crude nitrobenzene phase withdrawn from the spent acid. Analysis of the organic phase showed 94% mononitrobenzene, 5.9% benzene, 0.02% m-dinitrobenzene and 0.02% 2,6-dinitrophenol. Spent acid concentration was 70.48% sulfuric acid. No nitric acid was present.

EXAMPLE 2

A vigorously agitated insulated reaction vessel containing a mixed acid consisting of 5.2 percent nitric acid, 67.6% sulfuric acid and 27.2% water was heated to 60° C. Benzene in stoichiometric amount, was added thereto over a period of 0.15 minutes. The temperature increased to 106° C. during a total reaction time of 2.4 minutes. The organic phase was then separated from the residual sulfuric acid and the organic phase analyzed for m-dinitrobenzene. There was found to be 0.008% m-DNB or 80 ppm.

EXAMPLES 3–17

Following the procedure of Example 2, except that a 5% excess of benzene was used, a number of experiments were conducted as shown in Table 1.

TABLE 1

| Example | Mixed Acid % HNO₃ | Mixed Acid % H₂SO₄ | Mixed Acid % H₂O | Reaction Time, Min. | Reaction Temperature, °C Initial | Reaction Temperature, °C Final | Spent Acid (% H₂SO₄) | m-DNB % | 2,6-DNP % |
|---|---|---|---|---|---|---|---|---|---|
| 3 | 6.2 | 61.0 | 32.8 | 7.5 | 60 | 104 | 63.8 | ND** | 0.079 |
| 4 | 6.2 | 61.0 | 32.8 | 3.5 | 80 | 124 | 63.8 | ND | 0.12 |
| 5 | 6.2 | 64.0 | 29.8 | 2.25 | 60 | 112 | 67.0 | ND | 0.071 |
| 6 | 6.2 | 64.0 | 29.8 | 1.5 | 80 | 132 | 67.0 | 0.01 | 0.13 |
| 7 | 6.2 | 68.0 | 25.8 | 0.8 | 60 | 120 | 71.2 | 0.01 | 0/08 |
| 8 | 6.2 | 68.0 | 25.8 | 0.75 | 80 | 135 | 71.2 | 0.051 | 0.13 |
| 9 | 8.2 | 61.0 | 30.8 | 5.0 | 60 | 122 | 64.8 | NK | 0.11 |
| 10 | 8.2 | 61.0 | 30.8 | 3.5 | 80 | 135 | 64.8 | NS | 0.16 |
| 11 | 8.2 | 64.0 | 27.8 | 2.5 | 60 | 128 | 68.0 | ND | 1.10 |
| 12 | 8.2 | 64.0 | 27.8 | 1.75 | 80 | 145 | 68.0 | 0.036 | 0.18 |
| 13 | 8.2 | 68.0 | 23.8* | 0.8 | 60 | 132 | 72.2 | 0.09* | 0.12 |
| 14 | 8.2 | 68.0 | 23.8* | 1.0 | 80 | 148 | 72.2 | 0.38* | 0.19 |
| 15 | 5.2 | 68.0 | 26.8 | 1.75 | 80 | 123 | 70.6 | 0.035 | — |
| 16⁽¹⁾ | 4.0 | 70.2 | 25.8 | 1.0 | 90* | 124 | 72.3 | 0.11* | 0.127 |
| 17⁽¹⁾ | 4.0 | 70.2 | 25.8 | 10.0*** | 90 | 119 | 72.3 | 1.80 | 0.153 |

*Note: these examples are outside the scope of the invention; product does not meet specification.
**None detected
***Benzene addition time
⁽¹⁾1% benzene excess

We claim:

1. In an adiabatic process for the production of mononitro compounds, which are stable in the presence of hot sulfuric acid, from nitratable aromatic hydrocarbons or halogen substituted aromatic hydrocarbons, which are stable in the presence of hot sulfuric acid, wherein a mixed acid is contacted with up to a 10 percent stoichiometric excess of said nitratable aromatic hydrocarbon or halogen substituted aromatic hydrocarbon to form a reaction mixture, in such a manner that the heat of mixing, and the heat of reaction are substantially adsorbed by said reaction mixture, and said reaction mixture is then separated into two portions, one portion consisting of the mononitro compound and unreacted nitratable aromatic hydrocarbon or halogen substituted aromatic hydrocarbon and the other portion consisting substantially of hot aqueous sulfuric acid substantially free of nitric acid, and said portion of hot aqueous sulfuric acid is concentrated to its original concentration, wherein the improvement comprises: contacting said nitratable aromatic hydrocarbon or halogen substituted aromatic hydrocarbon with a mixed acid containing from about 5% to 8.5% nitric acid, about 60% to 70% sulfuric acid and not less than about 25% water, at a temperature in the range of about 40° C. to 80° C. for a period of about 0.5 to 7.5 minutes, whereby the temperature of the reaction mixture does not exceed about 145° C.

2. A process according to claim 1 conducted as a batch process.

3. A process according to claim 2 wherein the nitratable aromatic hydrocarbon or halogen substituted aromatic hydrocarbon is selected from the group consisting of: benzene, toluene, dimethylbenzene, halobenzene, naphthalene, methylnaphthalene, halonaphthalene, halotoluenes, and halomethylnaphthalenes.

4. A process according to claim 3 wherein the mixed acid contains from about 6 to 8% nitric acid, the initial reaction temperature is about 60°–75° C., the nitratable aromatic hydrocarbon or halogen substituted aromatic hydrocarbon is liquifiable in the temperature range from about 60°–75° C., and the reaction time is 0.5 to 3 minutes.

5. A process according to claim 4 wherein the nitratable aromatic hydrocarbon is benzene.

6. A process according to claim 1 conducted as a continuous process.

7. A process according to claim 6 wherein the nitratable aromatic hydrocarbon or halogen substituted aromatic hydrocarbon is selected from the group consisting of: benzene, toluene, dimethylbenzene, halobenzene, naphthalene, methylnaphthalene, halonaphthalene, halotoluenes, and halomethylnaphthalenes.

8. A process according to claim 7 wherein the mixed acid contains from about 6 to 8% nitric acid, the initial reaction temperature is about 60°–75° C., the nitratable aromatic hydrocarbon or halogen substituted aromatic hydrocarbon is liquifiable in the range of 60° to 75° C., and the reaction time is 0.5 to 3 minutes.

9. A process according to claim 8 wherein the nitratable aromatic hydrocarbon is benzene.

* * * * *